United States Patent [19]

Wellenstam

[11] Patent Number: 4,629,159
[45] Date of Patent: Dec. 16, 1986

[54] VALVE-PROVIDED CONNECTING DEVICE

[75] Inventor: Kjell I. Wellenstam, Göteborg, Sweden

[73] Assignee: Astra Meditec AB, Molndal, Sweden

[21] Appl. No.: 749,889

[22] Filed: Jun. 27, 1985

[30] Foreign Application Priority Data

Jan. 8, 1985 [SE] Sweden .................. 8500075

[51] Int. Cl.⁴ ............................. F16K 37/28
[52] U.S. Cl. ..................... 251/149.6; 137/614.18;
604/247; 604/323; 604/326; 604/905
[58] Field of Search ............... 137/614.18, 614.2, 843;
251/149.6; 604/247, 256, 323, 326, 335, 350, 905

[56] References Cited

U.S. PATENT DOCUMENTS

| | | |
|---|---|---|
| 839,912 | 1/1907 | Whelan .................. 137/877 |
| 2,949,929 | 8/1960 | Moore, Jr. et al. ........... 137/843 X |
| 3,476,142 | 11/1969 | Schultz .................. 137/614.2 X |
| 3,477,471 | 11/1969 | Mallinson .................. 137/614.18 |
| 3,610,268 | 10/1971 | Arutunoff .................. 137/614.18 X |
| 3,642,037 | 2/1972 | Cunningham . | |
| 3,729,023 | 4/1973 | Hammond .................. 251/149.6 X |
| 3,967,645 | 7/1976 | Gregory .................. 604/350 X |
| 4,354,523 | 10/1982 | Hochmuth et al. ........... 137/614.18 |

FOREIGN PATENT DOCUMENTS

| | | |
|---|---|---|
| 0038470 | 10/1981 | European Pat. Off. . |
| 0080379 | 1/1983 | European Pat. Off. . |
| 1616477 | 1/1971 | Fed. Rep. of Germany . |
| WO81/00512 | 8/1980 | PCT Int'l Appl. . |
| 2094151 | 9/1982 | United Kingdom . |
| 2118440 | 11/1983 | United Kingdom . |

Primary Examiner—A. Michael Chambers
Assistant Examiner—John C. Fox

[57] ABSTRACT

Valve-provided tube connecting device to connection with a liquid line intended to be connected to a patient, preferably for draining of body liquids. Said connection device consists of a drip chamber house, a connecting house containing a spring loaded valve body, which connecting house is designed to connection with a connector. The valve body consists of a conical upper sealing part, a guide part and a solid, conical lower sealing part. The device attained a closed system, which decreases the risk of bacteria infections and spillage.

8 Claims, 8 Drawing Figures

VALVE-PROVIDED CONNECTING DEVICE

DESCRIPTION

1. Technical Field

The present invention relates to a valve-provided tube connecting device to be connected with a liquid line intended to be connected to a patient either for draining of body liquids, e.g. in relation to collection of urine or surgical draining, or in the delivery of liquids in different infusion systems. A purpose of the invention is to achieve an effectively closed system to minimize the risk of bacterial infections, at the same time as the risk of spillage is minimized.

2. Background Art

Catheters are used as devices for patients who temporarily or permanently have lost their ability to control the urine draining from the urinary bladder. Such catheters are connected to urinary drainage bag with a welded tube and a connector of variable length. The drainage bag is exchanged at different intervals of time depending on the produced amount of urine, normally 3-4 times per day. The bag exchange is done by using a clip which is closed on a point above the disconnecting point in prinicpal to prevent leakage, and thereafter the bag is disconnected. However, this method suffers from several serious defects. The most grave defect is the discontinuation of the closed system and the strong increasing of the risk of intraluminar bacterial growth. The risk of spillage is great in spite of the clip, which makes the process a sloppy operation.

Previously in EP No. 0 080 379 a connector assembly for use in drainage system of body liquids consisting of a valve-provided socket part and a valve-provided plug part which are plugged together has been described.

3. Disclosure of the Invention

The present invention relates to a valve-provided tube connecting device of a new construction. Said valve-provided tube connecting device effectively maintains the closed system by closing the inlet upon either the disconnection of a drainage bag or at the connection of an infusion system. In that way the risk of bacteria and other contaminants entering and inside the system, with consequent dangerous and expensive bacteria infections is decreased. Such a closed system would save a lot of human pain, while at the same time reducing the cost of health service as a result of fewer patient infections. The present connecting device minimizes the risk of spillage and facilitates the sloppy and unpleasant operation of handling liquids such as urine.

The invention is explained in detail in the following with reference to an embodiment according to the enclosed drawings.

Figure 1:
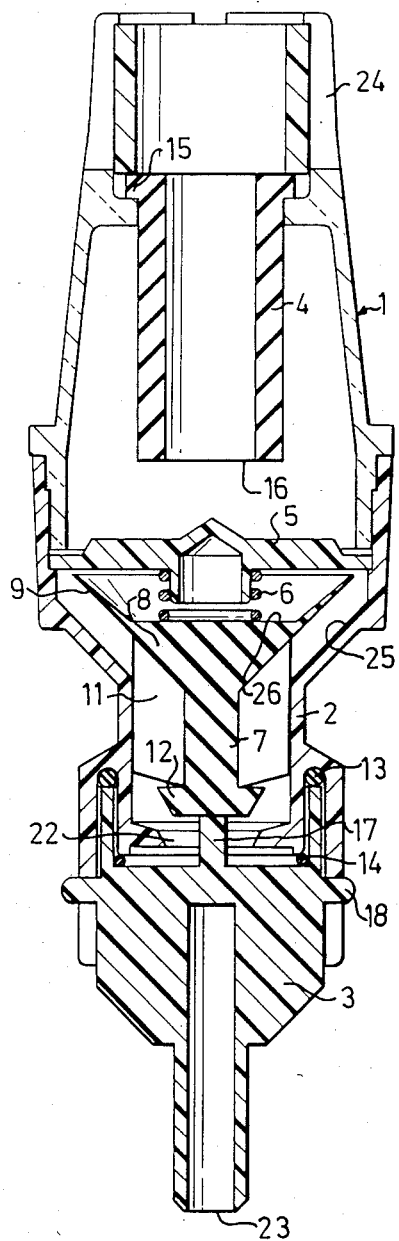
FIG. 1 shows a cross section of the connecting device in assembled position.

The connecting device consists of three units:

A drip chamber house (1) preferably with a non-return valve (4), a connecting house (2) with a spring loaded valve body (7), located downstream from the drip chamber house (1) a connector (3) designed for connecting with the connecting house (2).

The following description only exemplifies the invention in more detail and illustrates a suitable embodiment within a suitable field of use, but it is not a restriction of the invention.

A DETAILED DESCRIPTION OF THE FIGURES AND THE CONNECTING DEVICE

Figure 5:
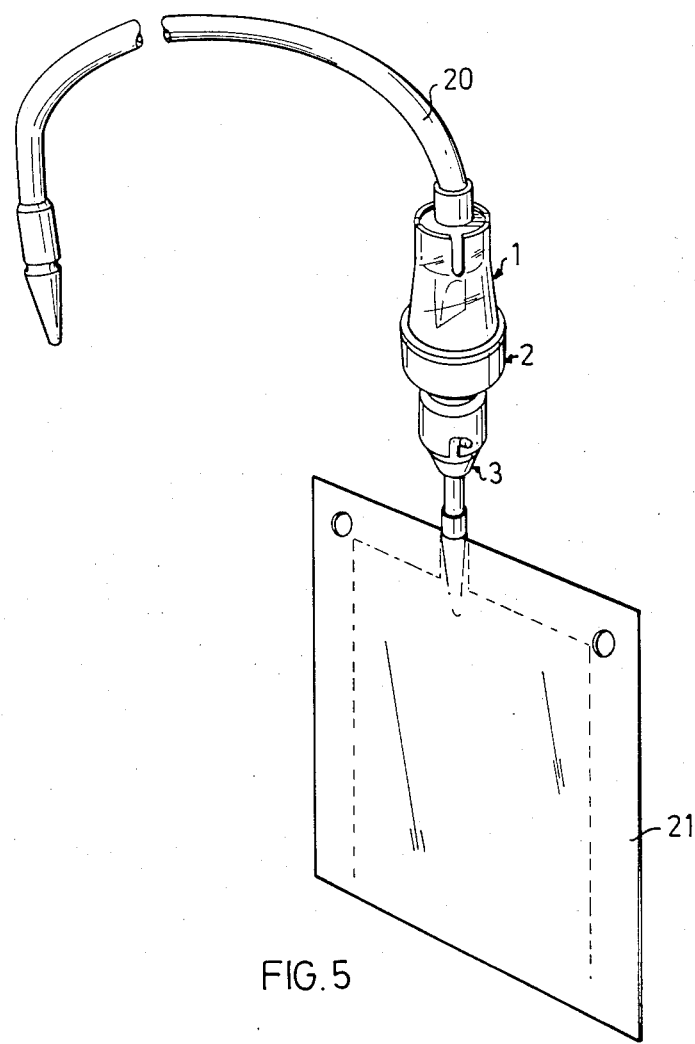
FIG. 5 shows a view of the connecting device inserted in a drainage system in outline.

Referring first to FIG. 5, there is shown a connecting device according to the invention. The connecting device consists of a drip chamber house (1) and a connecting house (2) to which connector (3) is connected. The drip chamber house (1) is connected at the upper end to a plug-provided inlet tube (20) which is used for drainage of body liquids, especially urine. At the lower end of the connecting device, the connector (3) is connected to a drainage bag (21).

The drip chamber house (1) is made of, e.g., transparent plastic, and, as shown in FIG. 1, is provided with a grooved socket (24) at the top to which the plug part of the inlet tube (20) can be attached. In the upper part of the drip chamber house (1) is located a non-return valve (4) to control the flow of the drainage liquid. The non-return valve (4) is preferably made of elastic, thin-walled silicon rubber.

Figure 4A:
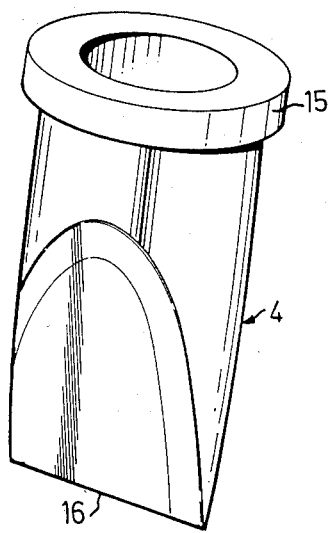
FIGS. 4A and 4B show the non-return valve.
Figure 4B:
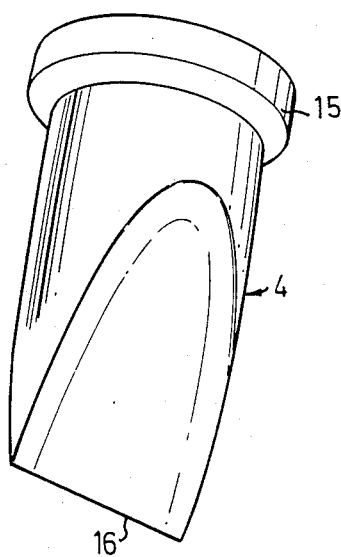

The non-return valve (4) (FIGS. 4A and 4B) has a collar (15) at the top which acts as a sealing-ring with the plug on inlet tube (20). The collar (15) also acts to suspend the non-return valve (4) in position within the drip chamber house (1). At the bottom of the non-return valve (4) is a narrow opening (16).

The lower end of the drip chamber house (1) is joined to the upper end of the connecting housing (2) by, e.g., ultrasonic welding or gluing. At the cylindrical upper end of the connecting house (2) there is an aperatured spring holder (5) which is preferably made of plastic. One end of a spring (6) is fastened to the underside of the spring holder (5). The other end of the spring (6) presses against a valve body (7) located within the connecting house.

Figure 3A:
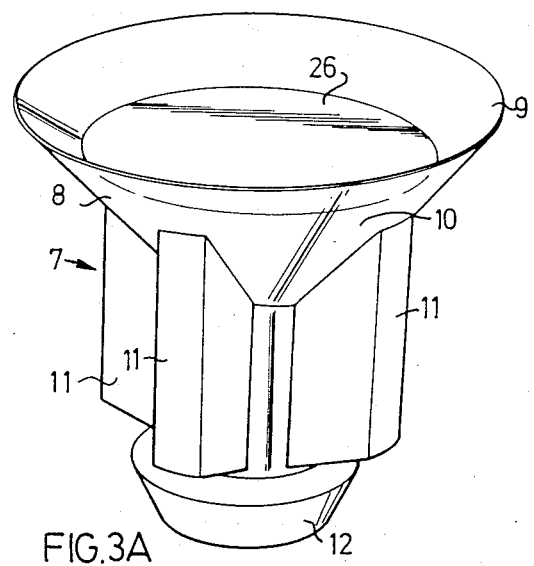
FIG. 3A shows the valve body, having a guide part designed with 4 wings.
Figure 3B:
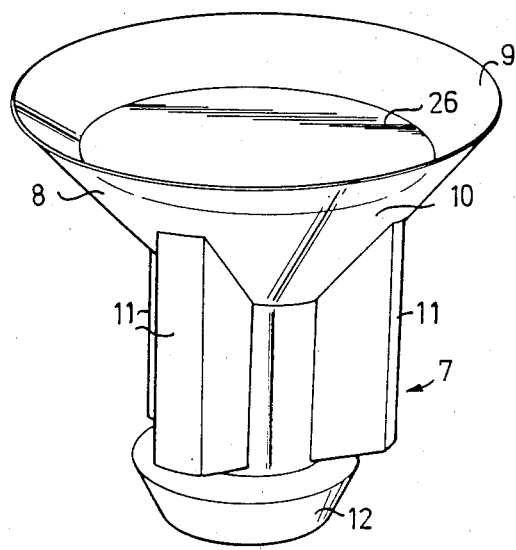
FIG. 3B shows the valve body, having a guide part designed with 3 wings.

The valve body (7) is made of an elastic material, preferably silicone rubber. The valve body (7) (FIGS. 3A and 3B) consists of an conical upper part (8), and a conical lower part, the foot (12). The upper conical part (8) consists of two sections, one thin-walled upper section (9) and one solid lower section (10). Guide part (11) are attached to the lower section (10) above the foot (12) and are fixed in radial direction and movable only in axial direction.

The guide parts (11) can be designed in different ways e.g. in the form of projecting wings from a central core or in form of a solid core provided with channels inside, wherein the liquids can flow. The projecting wings can be 2, 3, 4 or even more in number, preferably 3 or 4. The function of the guide parts (11) is to guide the valve body (7) striaght upwards by sliding against the vertical interior walls of the connecting house (2), while permitting liquid passage.

In the lower part of the connecting house are an outlet (22) for the liquid passage and grooves (19) for connecting with the projecting guide pins (18) of the connector (3) of the bayonet socket.

Figure 2A:
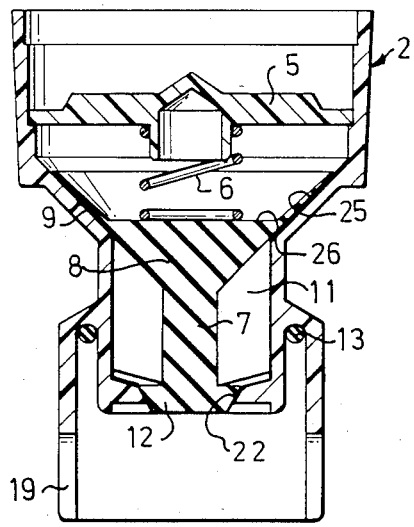
FIG. 2A shows a cross section of the connecting house in unassembled position.
Figure 2B:
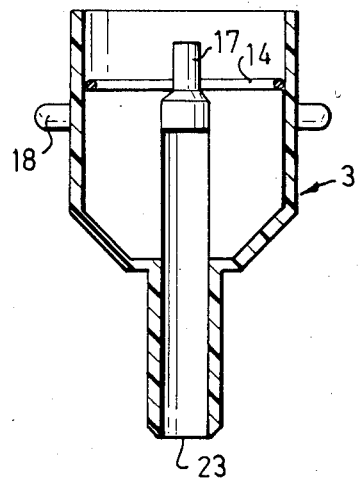
FIG. 2B shows a cross section of the connector in unassembled position.

As shown in FIG. 2B, the connector (3) is hollow and it is preferably made of plastic. Inside, the connector (3)

is provided with a central pin (17) mounted on e.g. a cross-bar (not shown), in order that the liquid passage is not prevented. The outlet at the bottom of the connector (23) opens in a drainage bag (21) for instance by attaching the lower tube formed part of the connector to a welded tube of the bag. A sealing ring (3) can be placed in the lower part of the connecting house or alternatively a sealing ring (14) can be placed along the cylindric interior surface of the connector. It is also possible that both sealing rings (13) and (14) exist simultaneously, to pevent leakage between the connecting house and the connector in assembled position. At the same time, the sealing rings bring about a slight pre-stressing when the bayonet socket is in connected position.

The connecting device according to the invention is in principle intended for non-recurring use. Accordingly, it is suitable that the drip chamber house (1), the connecting house (2), the connector (3) and the spring holder (5) be made of a plastic material e.g. an injection moulded thermoplastic such as styrenacylic nitrile (SAN). The drip chamber house is best made of a transparent plastic. The non-return valve, the valve body and the sealing rings are made of a soft, elastic, sealing material, e.g. silicone rubber, and they are manufactured in one piece by injection moulding or casting. The spring can best be made of stainless steel.

The drawings show the best way to carry out the invention as is anticipated today. The design of the valve-provided connecting device can be varied within the scope of the following claims and the idea of the invention.

THE CONNECTING DEVICE FUNCTIONS IN THE FOLLOWING WAY IN UNASSEMBLED I.E. CLOSED POSITION (FIG. 2)

Three sealing zones exist in the connecting house (2) when the device is unassembled, i.e. disconnected. The conical upper part of the valve body (8) seals against the connecting house in two different ways. The sealing is effected, partly by the drainage liquid pressing the thin-walled upper section (9) of the conical upper part of the valve body against the conical interior walls of the connecting house (25), and partly by pressing of the spring (6), which is installed in the lower part of the spring holder (5), against the interior bottom surface (26) of the solid lower section of the conical upper part of the valve body. A further sealing zone is the foot of the valve body (12), which by transmission of the spring pressure through the conical solid section and the guide part to the foot closes the outlet at the bottom of the connecting house (22) by the conical foot (12) lying close to the conical walls in the lower outlet of the connecting house.

THE CONNECTING DEVICE FUNCTIONS IN THE FOLLOWING WAY IN ASSEMBLED I.E. OPENED POSITION (FIG. 1)

When the guide pins (18) of the connector are entered and are locked in the grooves (19) of the bayonet socket of the connecting house, the following happens:

The system is opened by pressing the foot (12) of the valve body upwards with the central pin (17) of the connector. The whole valve body is guided straight upwards by sliding of the guide part (11) against the vertical interior walls of the connecting house. At this time, the outlet (22) at the sealing zones is opened to permit liquid passage.

The way of the liquid through the connecting device is the following:

The drainage liquid from the inlet tube (20) comes inside the drip chamber house (1) by the non-return valve (4). From there, the liquid passes through the aperatures in the spring holder (5), streaming down and getting into and beside the elevated valve body. The liquid continues down through the slit between the conical upper part (8) of the valve body and the conical interior walls (25) of the connecting house and through the channels (grooves) which exist in the guide part (11) and out through the outlet of the connecting house (22) which is opened, since the foot of the valve body has been pressed up. Then the liquid passes down through the hollow connector (3) and out by the lower outlet of the connector (23) out in the drainage bag (21).

I claim:

1. A valve-provided connecting device to be connected with a liquid line intended to be connected to a patient for draining body liquids, comprising a drip chamber house, a connecting house placed downstream of the drip chamber house and designed for connection with a connector, characterized in that said connecting house contains a spring loaded, elastic valve body consisting of a conical upper sealing part which consists of two sections, one thin-walled upper section and one solid lower section, a guide part having first and second ends, fixed in a radial direction and moveable only in an axial direction said conical upper sealing part being mounted on said first end, and a solid, conical lower sealing part mounted on said second end, wherein said thin wall upper section and said solid lower section on the conical upper sealing part respectively form two independent sealing zones and said lower sealing part forms a third independent sealing zone.

2. A valve-provided connecting device according to the claim 1, characterized in that the guide part of the valve body (11) has three or four wings.

3. A valve-provided connecting device according to the claim 1, characterized in that the drip chamber house (1) is provided with a non-return valve (4).

4. A valve-provided connecting device according to the claim 3, characterized in that the top of the non-return valve (4) is designed with a collar (5), which also acts as a sealing.

5. A valve-provided connection device according to the claim 3, characterized in that the bottom of the non-return valve has an opening gap (16) and is made of thin-walled, elastic rubber and injection moulded or casted in one piece.

6. A valve-provided connecting device according to the claim 1, characterized in that the connecting house (2) contains a spring holder (5) on the underside of which a spring (6) is fastened.

7. A valve-provided connecting device according to the claim 1, characterized in that the valve body (7) is arranged to be lifted by a centre pin (17) placed in a connector (3) when connected to the connecting house (2).

8. In a device for draining body fluids from a patient said device comprising a catheter for withdrawing body fluids, a reservoir for receiving said body fluids and a connector joining said catheter and said reservoir, said connector comprising a first member and a second member the improvement wherein:

(A) said first member comprises an enclosed chamber having a first end and a second end, and having an upper portion and a lower portion, said upper portion being enclosed by said first end and said lower portion terminating in said second end,
(1) said first end having an inlet connected to said catheter for receiving body fluids therefrom;
(2) said upper portion being enlarged relative to said lower portion and forming a drip chamber for receiving body fluids from said catheter;
(3) a tapered section having a substantially frusto-conical shape joining said upper portion and lower section, said tapered section forming a first valve seat means;
(4) an enclosing diaphragm across the second end in said lower portion, said diaphragm having an opening to permit said body fluids to leave said first member, said opening forming a second valve seat means;
(5) said lower section of said first member being a substantially cylindrical section joining said first valve seat means and said diaphragm;
(6) a valve body disposed within said lower section having a substantially frusto-conical first seal and a second seal, said seals being joined together and held in spaced relationship from each other by a spool member;
  (i) the spool member having a plurality of vanes extending to and being in slideable contact with the cylindrical section of said lower portion whereby said spool member permits displacement of said valve body in only a substantially axial direction between an open position and a closed position;
  (ii) said first valve seal member having a thin walled upper section and a solid lower section which are dimensioned to form two sealing contacts with first valve seat means when said valve body is in the closed position and said second valve seal member being dimensioned to form sealing contact with said second valve seat means when said valve body is in the closed position and said spool member being dimensioned to space said valve seal members from each other such that both valve seal members are concurrently engaged and sealed against the respective valve seats when said spool is moved into the closed position;
(7) a spider member disposed across the upper portion of said chamber; and
(8) spring means extending between said spider member and said valve body for urging said valve body into its closed position; and
(B) said second member has
(1) a tubular passageway having a first end and a second end, said first end adapted to engage the lower portion of said first member when said first and second members are coupled and adapted to receive body fluids from the hole in said diaphragm and said second end being operably connected to said reservoir;
(2) a spider means extending across said first end; and
(3) a prong extending from said spider means toward the opening of said first end, said prong engaging the valve body within said second member when said first and second members are coupled together, and maintaining said valve body in its open position.

* * * * *